US00PP35037P2

(12) United States Plant Patent
Jenkins

(10) Patent No.: US PP35,037 P2
(45) Date of Patent: Mar. 14, 2023

(54) PEPPERMINT PLANT NAMED 'PALISADE'

(50) Latin Name: ***Mentha* x *piperita***
Varietal Denomination: Palisade

(71) Applicant: Essex Laboratories, LLC, Napavine, WA (US)

(72) Inventor: Christopher Jenkins, Salem, OR (US)

(73) Assignee: ESSEX LABORATORIES, LLC, Napavine, WA (US)

( * ) Notice: Subject to any disclaimer, the term of this patent is extended or adjusted under 35 U.S.C. 154(b) by 0 days.

(21) Appl. No.: 17/491,034

(22) Filed: Sep. 30, 2021

(51) Int. Cl.
*A01H 5/12* (2018.01)
*A01H 6/50* (2018.01)

(52) U.S. Cl.
USPC ..... Plt./259
CPC ..... *A01H 6/504* (2018.05)

(58) Field of Classification Search
USPC ..... Plt./259
CPC ..... A01H 5/02; A01H 5/12
See application file for complete search history.

*Primary Examiner* — Kent L Bell
(74) *Attorney, Agent, or Firm* — Armstrong Teasdale LLP

(57) ABSTRACT

Peppermint plant selection 18-14-185, denominated 'Palisade' peppermint is a new *Mentha* x *piperita* cultivar that produces an essential oil different in composition than commercially grown mint varieties known to the Inventor. The essential oil is similar to standard Peppermint plant oil in components composition but differs substantially in the ratio of said components. Organoleptically, it differs from typical peppermint oil. It is more resistant to *Verticillium dahliae* mint wilt than current commercially grown varieties. Furthermore, 'Palisade' produces an oil type that varies minimally in oil profile based on plant maturity.

3 Drawing Sheets

Latin name of the genus and species: *Mentha* x *piperita*.
Variety denomination: 'PALISADE'.

TYPE OF PLANT AND NAME OF VARIETY

The present invention relates to a new and distinct variety of peppermint plant developed in Salem, Oreg., from a parent of the species *Mentha* x *piperita*. The new mint variety will be identified as 'Palisade'.

BACKGROUND OF INVENTION

'Palisade' originated as a seedling from an open pollinated polyploid *M. piperita* seedling parent, identified as 15-34-2, in Salem, Oreg. Seedling 15-34-2 was selected in 2015 from a population of fertile *M. piperita* plants. The parent to 'Palisade' was one of several Peppermint plant lines in a polycross breeding system composed of selected male and female fertile polyploid genotypes.

DISCOVERY AND ASEXUAL REPRODUCTION

This new Peppermint plant was developed in a Peppermint plant breeding program in which the primary objective was to develop a Peppermint plant variety having a specific oil composition, acceptable yield, and resistance to Peppermint plant diseases. Selection 'Palisade' has an equivalent oil yield to the control variety 'Black Mitcham' (Not Patented) in test plots since 2019. This plant was selected from a population of Peppermint plant seedlings in research plots on land in Salem, Oreg., and initially identified as 18-14-185.

'Palisade' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. The same propagation techniques of tip cuttings or stolon sections are used with 'Palisade' as with commercial mint cultivation. 'Palisade' produces a high number of stolons to allow propagation by this means. The inventor has conducted asexual propagation of 'Palisade' for greenhouse and field planting in Salem, Oreg., each year since 2018 and the genotype comes true to form with each generation.

The distinguishing traits present in 'Palisade' remain constant in the asexually produced plants. Resulting propagules remain stable in appearance, oil quality, and other characteristics from the original plant. Any minor observed differences can be attributed to variable environmental factors, such as climate, soil type, nutrient, or water regime.

SUMMARY OF THE INVENTION

Mint selection 18-14-185, denominated 'Palisade' is a new *Mentha* x *piperita* cultivar that produces an essential oil different in composition than commercially grown Peppermint plant varieties known to the Inventor. The essential oil is similar to standard Peppermint plant oil in components composition but differs substantially in the ratio of said components. Organoleptically, it differs from typical peppermint oil. It is more resistant to *Verticillium dahliae* mint wilt than current commercially grown varieties. Furthermore, 'Palisade' produces an oil type that varies minimally in oil profile based on plant maturity.

BRIEF DESCRIPTION OF THE FIGURES

The accompanying color figures show typical greenhouse and vegetative growth of 'Palisade' and depicts the color as nearly true as reasonably possible.

DESCRIPTION OF PLANT

Figure 1:
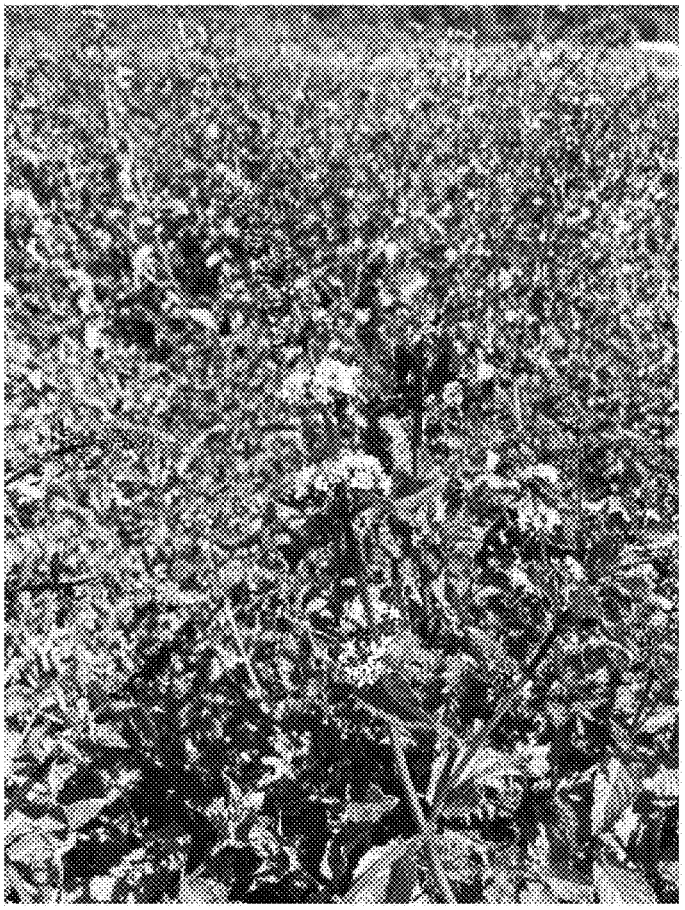
FIG. 1 shows the flower spike of 'Palisade'.

My new Peppermint plant improves upon and is distinct from other Peppermint plants in several characteristics, including but not limited to, the following:

1. The ability to produce an essential oil different in composition but with similar components as 'Black Mitcham' peppermint
2. A level of resistance to mint wilt (*Verticillium dahliae*) greater than that of its parent, 15-34-2, and 'Black Mitcham' peppermint
3. An early spring growth similar to 'Black Mitcham' peppermint but with an earlier maturity for desirable chemical composition of its essential oil. The ratio of oil components changes minimally with plant maturity as compared to its parent, 15-34-2, and 'Black Mitcham' peppermint The essential oil extracted from 'Palisade' has the same components as that of commercial oil produced by 'Black Mitcham' peppermint as illustrated in Table 1. However, the ratio of oil components differs between the commercial peppermint oil and that of 'Palisade'. The concentration of menthone and menthol in the oil of 'Palisade' is lower than that of 'Black Mitcham' and its parent, 15-34-2. The amount of menthofuran in the oil of 'Palisade' is substantially higher than that of 'Black Mitcham' and 15-34-2. Organoleptically, the oil of 'Palisade' is different from that of 'Black Mitcham' and 15-34-2, reflecting the difference in oil component ratios.

TABLE 1

Composition of 'Palisade' Oil from Test Plots v. 'Black Mitcham' Oil from Test Plots v. '15-34-2' Oil from Test Plots

| Essential Oil Components | 2020 Test Plot 'Palisade' | 2020 Test Plot 'Black Mitcham' | 2017 Test Plot '15-34-2' |
|---|---|---|---|
| 1-Limonene | 2.47 | 2.48 | 2.98 |
| 1,8-Cineole | 4.09 | 4.69 | 5.68 |
| Trans-Menthone | 4.41 | 15.13 | 9.02 |
| Menthofuran | 61.03 | 7.42 | 32.37 |
| Cis-Menthone | 0.69 | 2.13 | 1.56 |
| Menthyl acetate | 1.87 | 3.86 | 4.63 |
| Neo-menthol | 0.62 | 3.44 | 2.89 |
| B-caryophyllene | 0.87 | 2.73 | 2.51 |
| Menthol | 7.87 | 35.95 | 22.72 |
| Pulegone | 4.45 | 3.82 | 2.67 |
| Germacrene-D | 1.99 | 3.50 | 1.70 |

The numbers listed in the above table are percentages based upon the analysis of the respective mint oils by gas chromatography.

TAXONOMIC DESCRIPTION OF 'PALISADE'

This new Peppermint plant, under greenhouse and field growing conditions, is a bush type plant with lateral branches at each node of the main stem. The height of 'Palisade' will vary based on fertilizer, soil quality, and water application, amongst other known factors that affect growth patterns. 'Palisade' is between 0.3 and 0.5 m in width at mid-stem, and 0.8 to 1.1 m in height when grown in a greenhouse environment. Field grown 'Palisade' has a width of 0.3 to 0.5 m and a height of 0.7 to 1.1 m. Typical/observed internodal stem length is 31.5 mm-45.7 mm. Secondary and tertiary branching occurs to form a compact growth habit. When 'Palisade' is mature and ready for harvest, the main stem at mid-plant (approximately between the eleventh and twelfth node) is 3.2-4.5 mm in width. The secondary and tertiary branch stems are 2.3-2.7 mm and 1.0-1.4 mm in width, respectively. The stems are square, glabrous, and a green color that matches the 144A green group. All colors are described according to The Royal Horticulture Society Colour Chart, $5^{th}$ edition.

Figure 2:
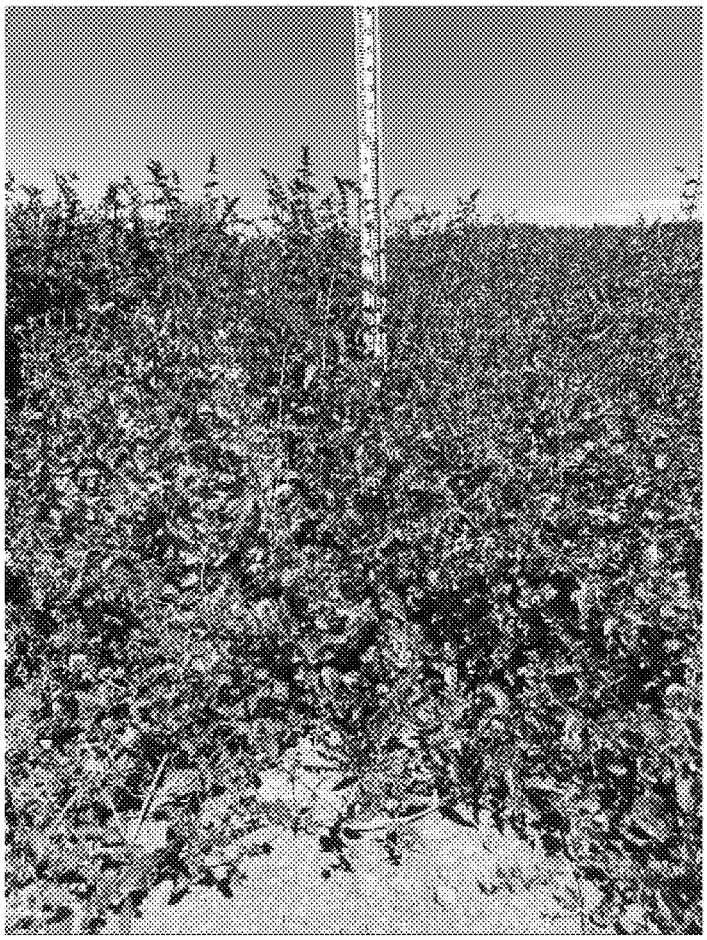
FIG. 2 shows the mature plant growth habit of 'Palisade'.
Figure 3:
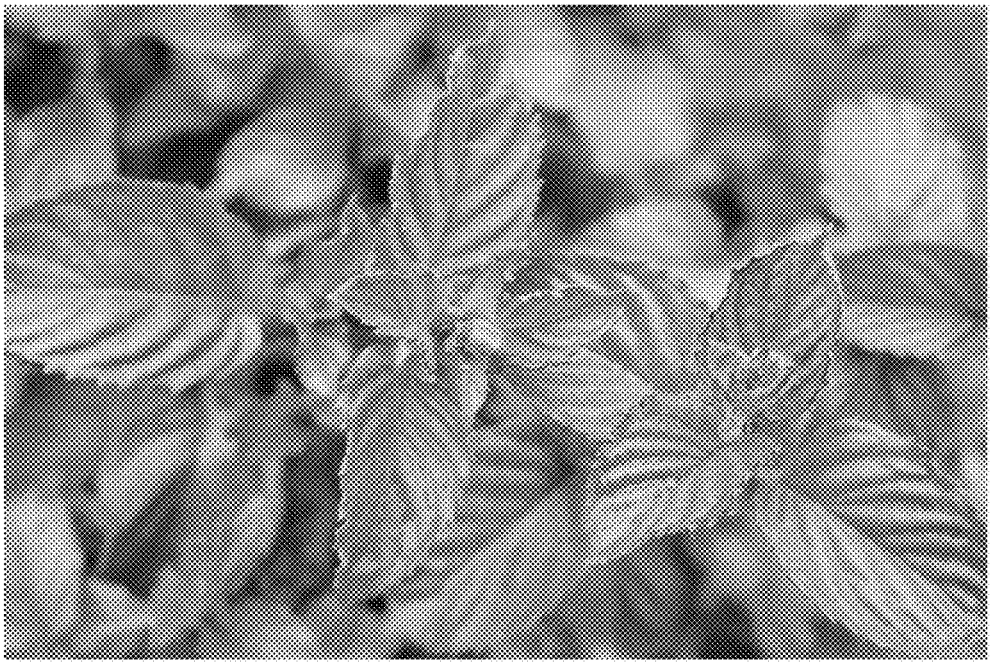
FIG. 3 shows the mature leaves of 'Palisade'.
Figure 4:
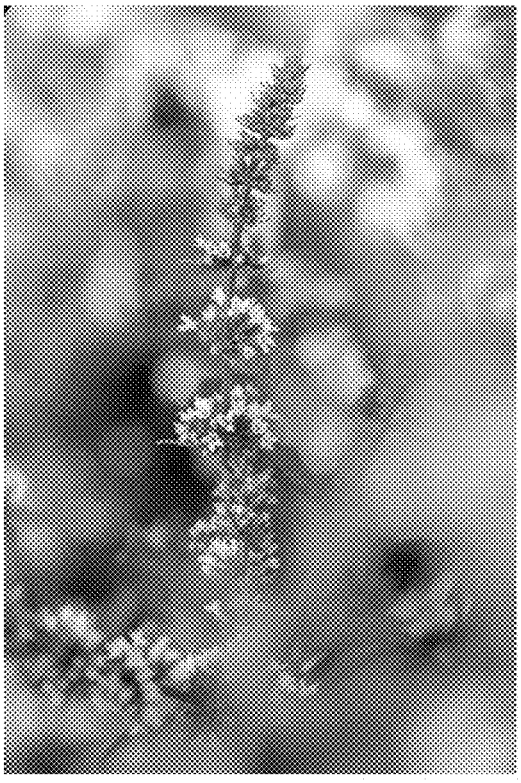
FIG. 4 shows the capitate flowers of 'Palisade'.

Mature leaves at the bottom of the plant are ovate to elliptical, as are leaves on secondary branch stems. The young, upper leaves are ovate to lanceolate in shape (FIG. 2). The adaxial leaf surface is glabrous. The abaxial leaf surface is sub-glabrous with oil glands distributed across the surface. Mid-main stem leaf size is 33-39 mm in width and 55-59 mm in length. Leaf size on secondary branches is 17-23 mm in width and 31-38 mm in length. Leaf petioles are sub-glabrous on the main stem leaves and petioles are light green in color, matching the 138B green group. Petioles on main stem leaves are 9.2-11.9 mm in length while petioles on secondary branch stem leaves are 3.6-5.3 mm in length. Leaves on upper, mid-main, and lower stem are serrated, with the main stem leaves having from 15-17 teeth, and the secondary branch leaves having from 8-9 teeth, on each side. The adaxial leaf is dark green in color, matching N137B in the green group classification. The color of the abaxial leaf surface is a yellow-green color that matches the 147B, yellow-green group. The leaf has 6-8 lateral veins that are arranged in an arcuate veination pattern. Typical/observed leaves from lower, mid-main, and upper stem display a cuspidate leaf apex. Typical/observed leaves from lower and mid-main stem display an obtuse leaf base, while leaves from upper stem display an acute leaf base. Leaf veins are 64A Red-Purple Group as matched to The Fifth Edition Royal Horticultural Society Colour Chart. Petal shape is a complex of five petals fused into a two-lipped corolla. Texture is sub-glabrous.

The inflorescence is raceme, with a 5-13 mm in length spike and capitate flowers developing at nodes of raceme. The average number of flowers per inflorescence of 'Palisade' is from 23-50, with the average flower length being from 5.1 mm to 8.0 mm and the average flower width being from 2.2 mm to 3.1 mm.

The capitate flowers are from 15.5-20.1 mm in width and 19.9-24.9 mm in length. The flowers consist of five petals fused into a two lipped corolla. Both the inner and outer surfaces of the corolla are violet in color, ranging from 85C to 85D in the violet group. The calyx is 3.7-4.2 mm in length and about 1.5-1.7 mm in diameter. Both the inner and outer surface of the calyx are generally yellow-green, matching the 144C yellow-green group. Additionally, the surface texture of the calyx of 'Palisade' is hairy and rough. Petal base is acute and apex is obtuse. Petal margin is entire (even, smooth throughout). Peduncles are 2 mm in length, 0.1-0.2 mm diameter, sub-glabrous texture, and 64A Red-Purple Group. Pedicels are 1.5 mm in length, 0.1-0.2 mm diameter, sub-glabrous texture, and 64A Red-Purple Group. The gynoecium consists of a single pistil with two lobed stigma that is exserted. The androecium consists of four stamens, each with a distinct filament and anther. The bloom season for 'Palisade' under field conditions is in July and August.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosures as come within known or customary practice in the art to which the invention pertains and as may be applied to the essential features hereinbefore set forth, and as fall within the scope of the invention and the limits of the appended claim.

I claim:

1. A new and distinct variety of peppermint plant named 'Palisade', substantially as illustrated and described.

* * * * *